US010210667B2

(12) United States Patent
Jin

(10) Patent No.: US 10,210,667 B2
(45) Date of Patent: Feb. 19, 2019

(54) DISPLAYING 3D IMAGE WITH A PLURALITY OF SURFACE IMAGES AT DEPTHS OF INTEREST

(71) Applicant: Ewoosoft Co., Ltd., Gyeonggi-do (KR)

(72) Inventor: Youngkyu Jin, Gyeonggi-do (KR)

(73) Assignee: Ewoosoft Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/766,856

(22) PCT Filed: Feb. 8, 2014

(86) PCT No.: PCT/KR2014/001081
§ 371 (c)(1),
(2) Date: Aug. 10, 2015

(87) PCT Pub. No.: WO2014/123396
PCT Pub. Date: Aug. 14, 2014

(65) Prior Publication Data
US 2015/0374316 A1    Dec. 31, 2015

(30) Foreign Application Priority Data
Feb. 8, 2013    (KR) .................. 10-2013-0014496

(51) Int. Cl.
*A61B 6/03*    (2006.01)
*A61B 6/00*    (2006.01)
(Continued)

(52) U.S. Cl.
CPC ............ *G06T 19/20* (2013.01); *A61B 6/032* (2013.01); *A61B 6/14* (2013.01); *A61B 6/463* (2013.01);
(Continued)

(58) Field of Classification Search
None
See application file for complete search history.

(56) References Cited

U.S. PATENT DOCUMENTS 5,371,778 A    12/1994   Yanof et al.
5,734,384 A    3/1998    Yanof et al.
(Continued)

FOREIGN PATENT DOCUMENTS

KR    20-0303415 Y1    2/2003
KR    10-0947826 B1    3/2010
(Continued)

OTHER PUBLICATIONS

Korean Intellectual Property Office, International Search Report of International Application No. PCT/KR2014/001081, dated May 20, 2014.
(Continued)

*Primary Examiner* — Said Broome
(74) *Attorney, Agent, or Firm* — IP Legal Services, LLC

(57) ABSTRACT

The disclosure is related to a display device that may produce and display a predetermined internal surface (e.g., a predetermined plane view) of an object according to a user input designating a depth thereof. Such display device may include a data storage, a user input interface, a processor, and an image display. The data storage may be configured to store image data. The user input interface may be configured to receive a request from a user. The processor may be configured to generate image data for a 3D image with internal surface images at one or more depths in response to the user request. The image display may be configured to display the 3D image with internal surfaces at each depth.

4 Claims, 10 Drawing Sheets

(51) Int. Cl.
  *A61B 6/14* (2006.01)
  *G06T 19/20* (2011.01)
  *G06T 7/00* (2017.01)
  *G06T 15/00* (2011.01)
  *G06T 17/00* (2006.01)
  *G09G 5/14* (2006.01)

(52) U.S. Cl.
  CPC .............. *A61B 6/466* (2013.01); *A61B 6/467* (2013.01); *A61B 6/5223* (2013.01); *G06T 7/0012* (2013.01); *G06T 15/00* (2013.01); *G06T 17/00* (2013.01); *G09G 5/14* (2013.01); *G06T 2207/10081* (2013.01); *G06T 2207/10116* (2013.01); *G06T 2207/30036* (2013.01); *G06T 2210/41* (2013.01); *G06T 2219/028* (2013.01); *G09G 2380/08* (2013.01)

(56) References Cited

U.S. PATENT DOCUMENTS

| | | | |
|---|---|---|---|
| 6,633,789 B1* | 10/2003 | Nikolskiy | G06F 19/321 433/2 |
| 6,664,986 B1 | 12/2003 | Kopelman et al. | |
| 8,199,988 B2 | 6/2012 | Marshall et al. | |
| 2003/0199769 A1* | 10/2003 | Podoleanu | A61B 3/102 600/476 |
| 2005/0149877 A1* | 7/2005 | Rice | A61B 5/0059 715/764 |
| 2006/0203959 A1 | 9/2006 | Spartiotis et al. | |
| 2007/0025642 A1 | 2/2007 | Buckland et al. | |
| 2007/0287916 A1 | 12/2007 | Kim et al. | |
| 2008/0019477 A1 | 1/2008 | Spartiotis et al. | |
| 2008/0063139 A1 | 3/2008 | Pantsar et al. | |
| 2008/0181477 A1 | 7/2008 | Izatt et al. | |
| 2009/0191503 A1 | 7/2009 | Matov et al. | |
| 2009/0316966 A1 | 12/2009 | Marshall et al. | |
| 2009/0323891 A1 | 12/2009 | Borghese et al. | |
| 2010/0142673 A1 | 6/2010 | Pantsar et al. | |
| 2010/0208866 A1 | 8/2010 | Spartiotis et al. | |
| 2010/0246761 A1 | 9/2010 | Pantsar et al. | |
| 2010/0255445 A1* | 10/2010 | Gantes | A61C 1/084 433/173 |
| 2011/0033026 A1 | 2/2011 | Ulrici et al. | |
| 2011/0075946 A1 | 3/2011 | Buckland et al. | |
| 2011/0102549 A1 | 5/2011 | Takahashi | |
| 2011/0144499 A1 | 6/2011 | Yoo et al. | |
| 2011/0172534 A1 | 7/2011 | Kim | |
| 2011/0282205 A1 | 11/2011 | Kim | |
| 2013/0202176 A1 | 8/2013 | Izatt et al. | |
| 2013/0230818 A1 | 9/2013 | Matov et al. | |

FOREIGN PATENT DOCUMENTS

| | | |
|---|---|---|
| KR | 10-1117930 B1 | 2/2012 |
| KR | 10-1126891 B1 | 3/2012 |
| KR | 10-1183767 B1 | 9/2012 |
| WO | 98/53428 A1 | 11/1998 |

OTHER PUBLICATIONS

Korean Intellectual Property Office, Written Opinion of International Application No. PCT/KR2014/001081, dated May 20, 2014.
Korean Intellectual Property Office, International Search Report of International Application No. PCT/KR2014/001080, dated May 23, 2014.
Korean Intellectual Property Office, Written Opinion of International Application No. PCT/KR2014/001080, dated May 23, 2014.

* cited by examiner

[Fig. 1]
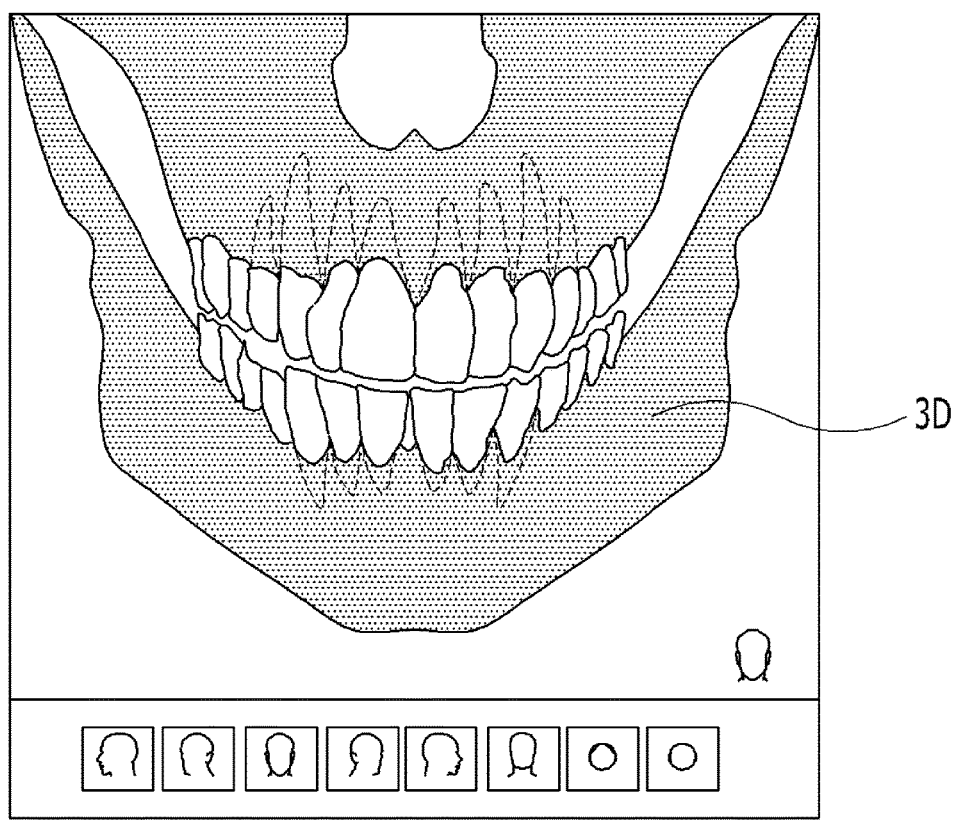

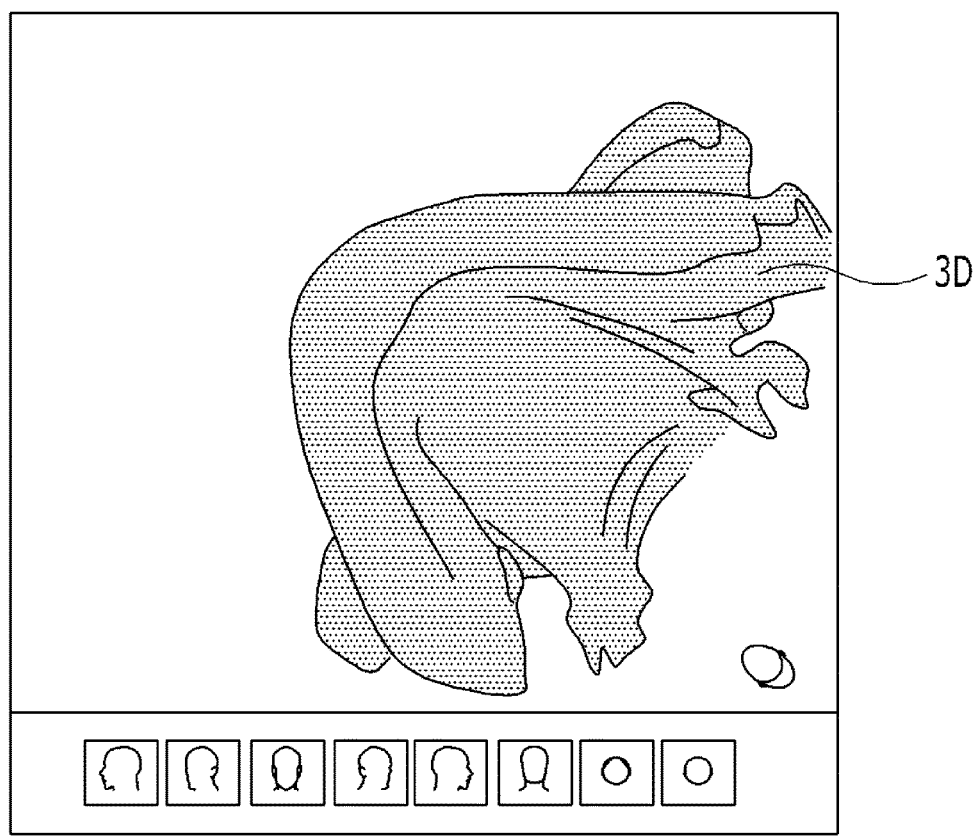
[Fig. 2]

[Fig. 3]
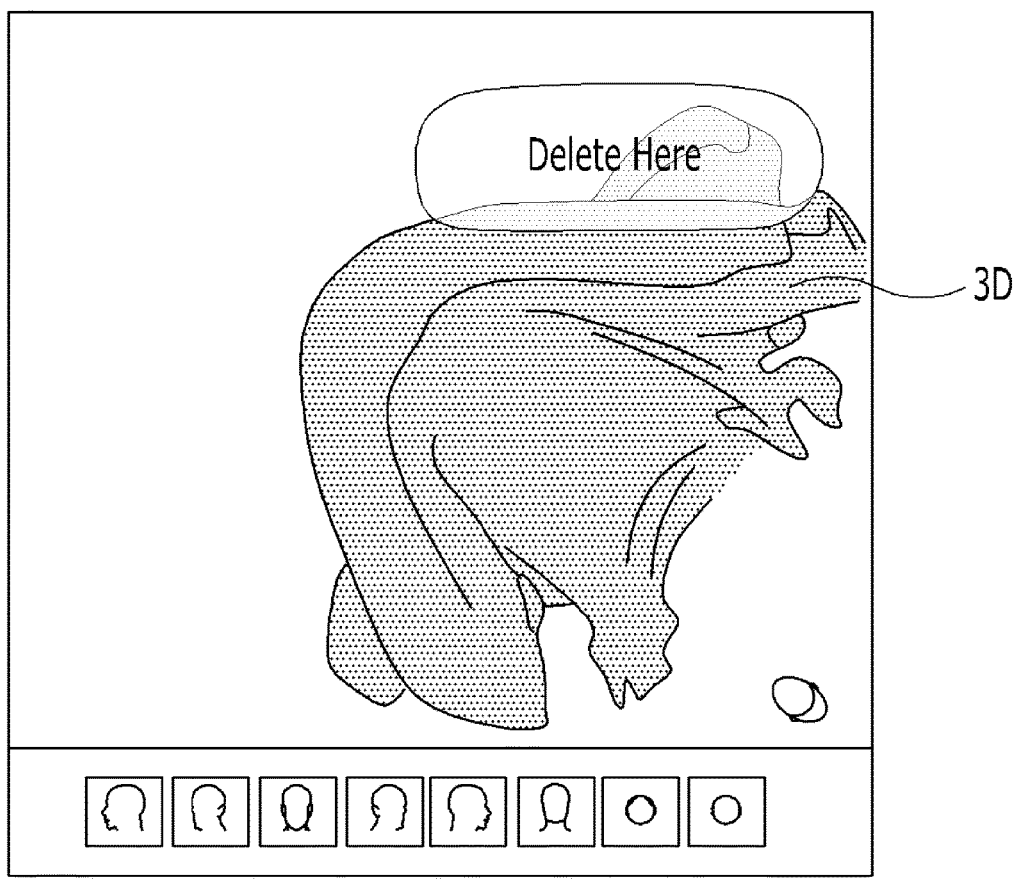

[Fig. 4]
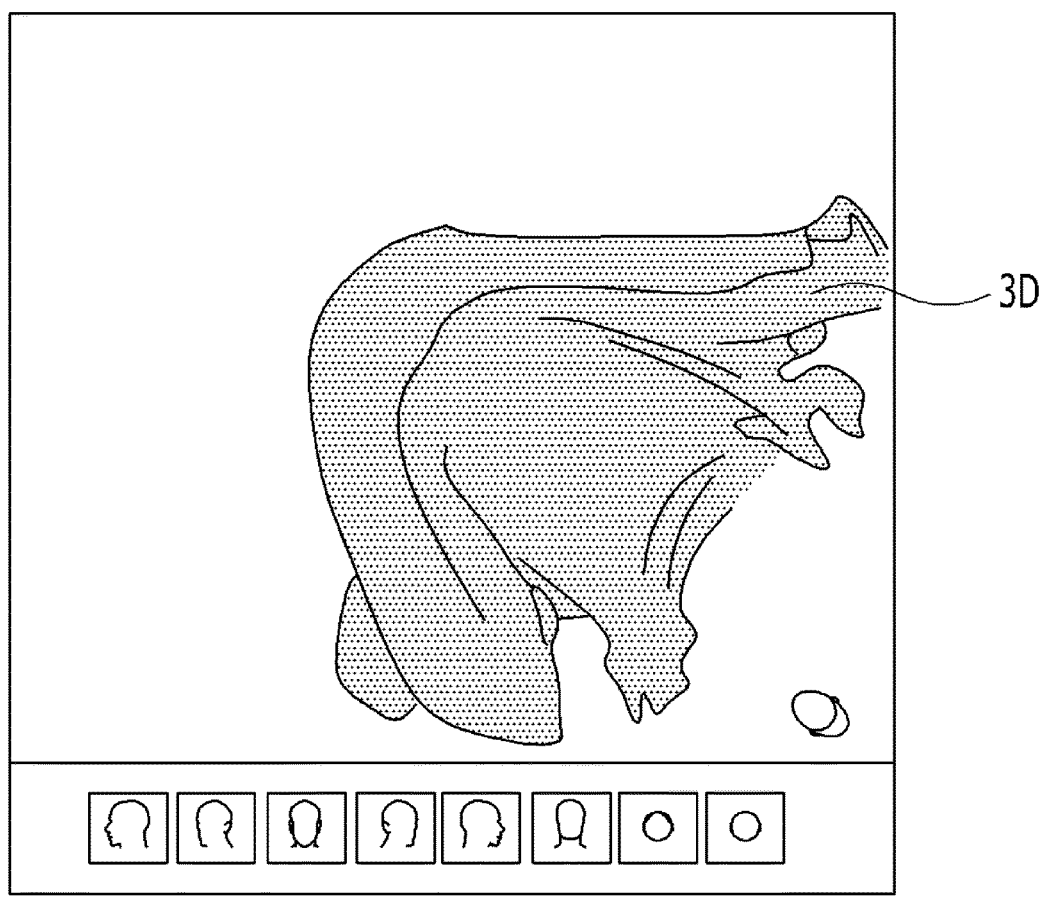

[Fig. 5]
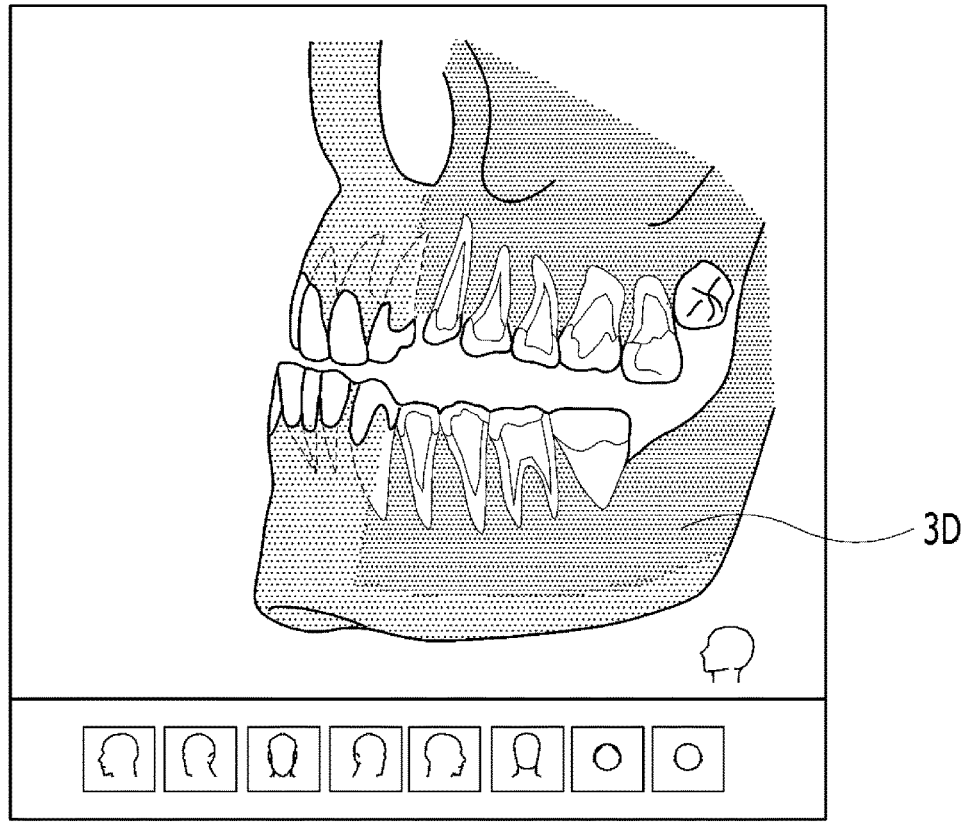
[Fig. 6]
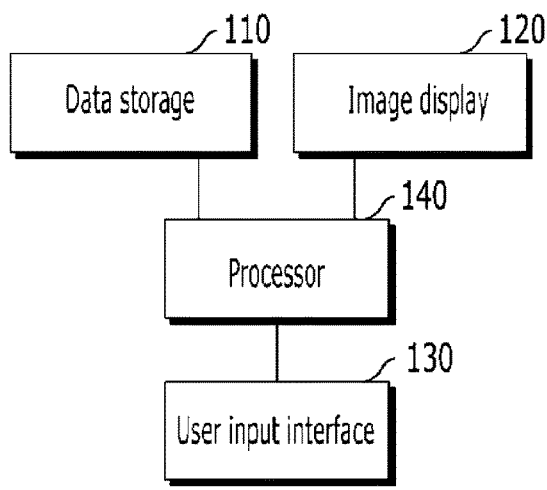

[Fig. 7]
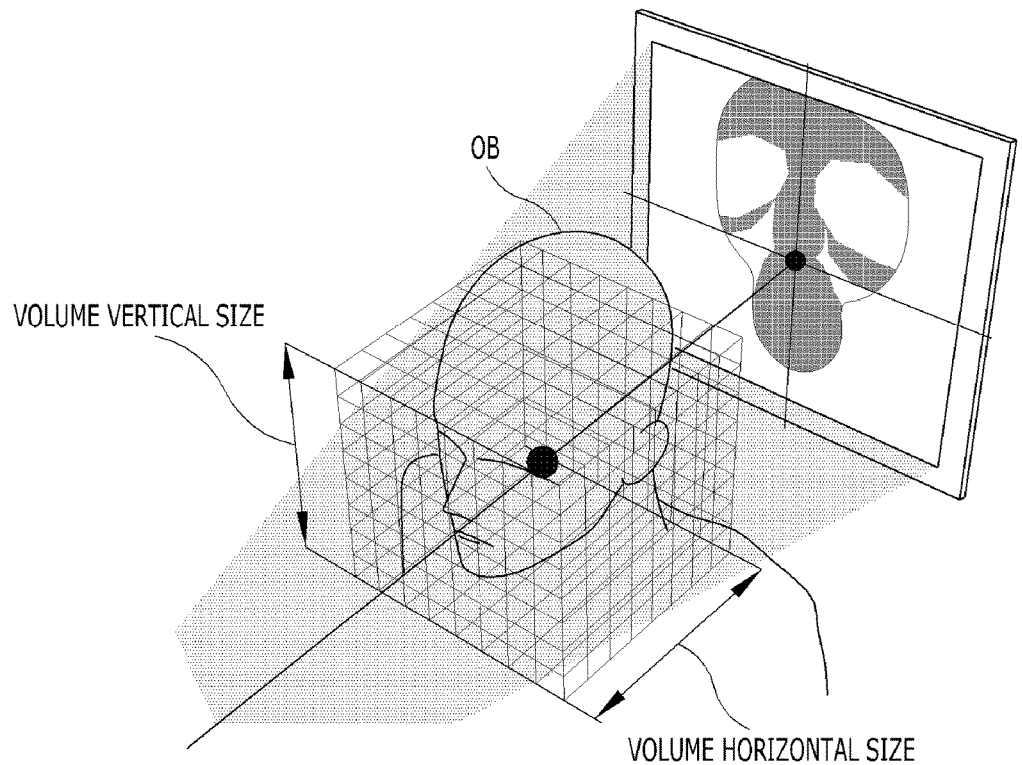
[Fig. 8]
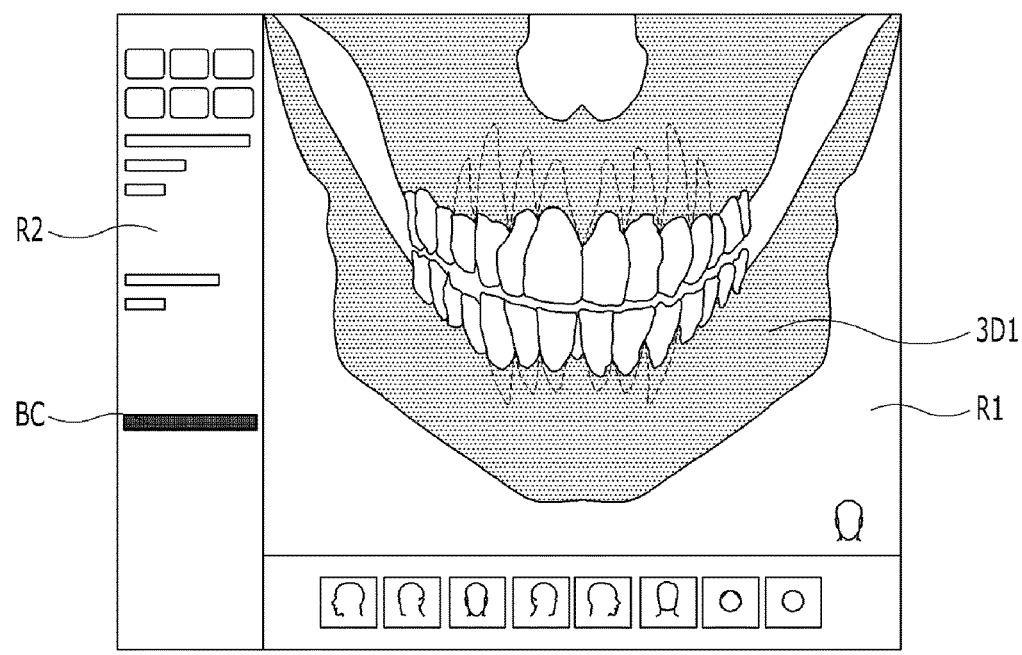

[Fig. 9]
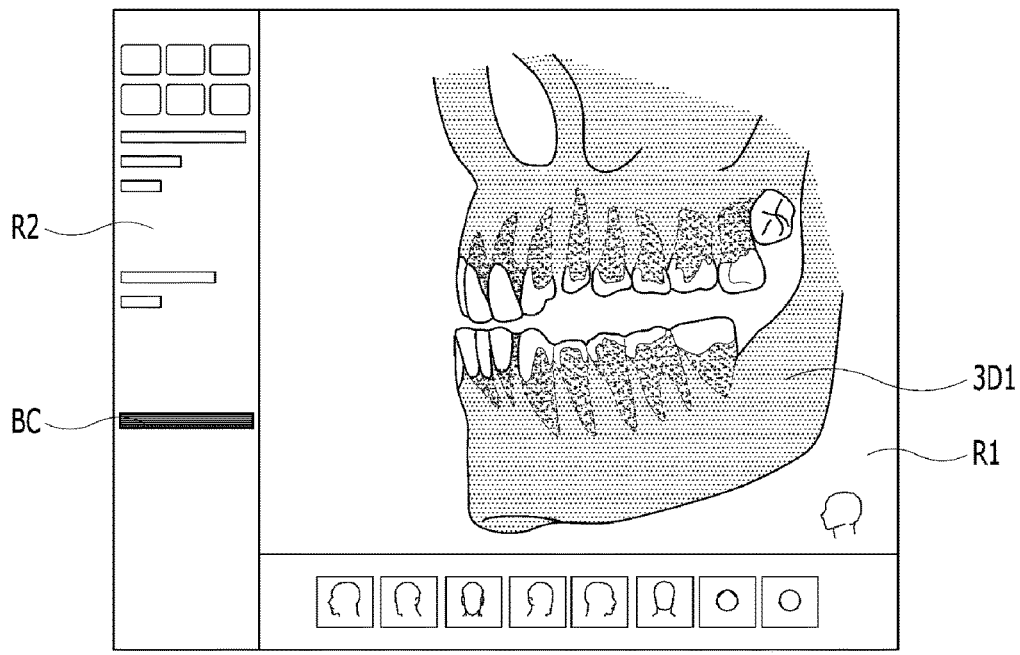
[Fig. 10]
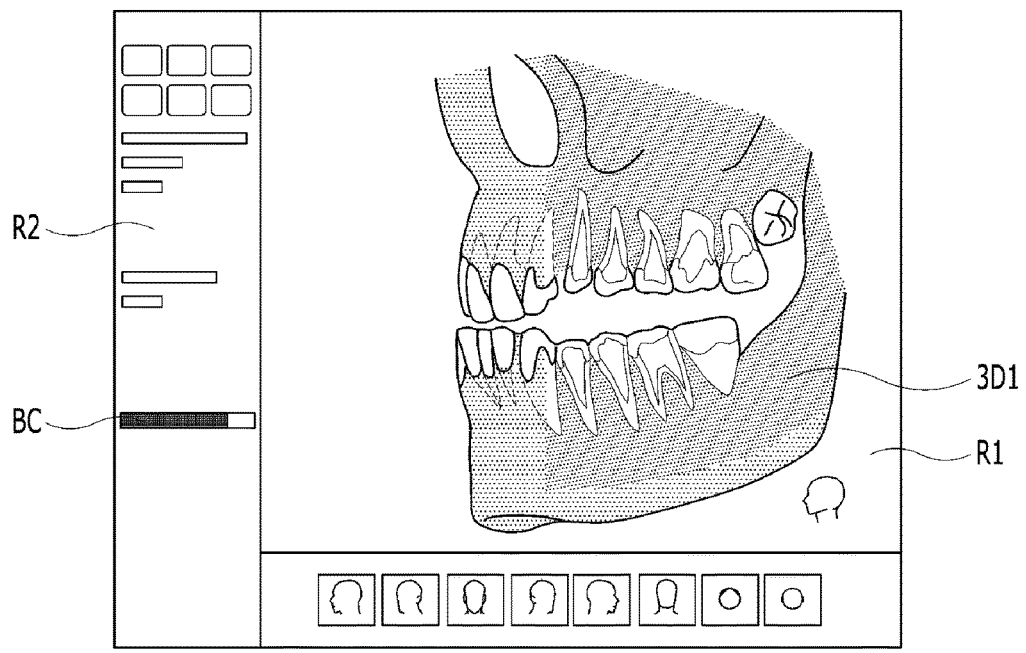

[Fig. 11]
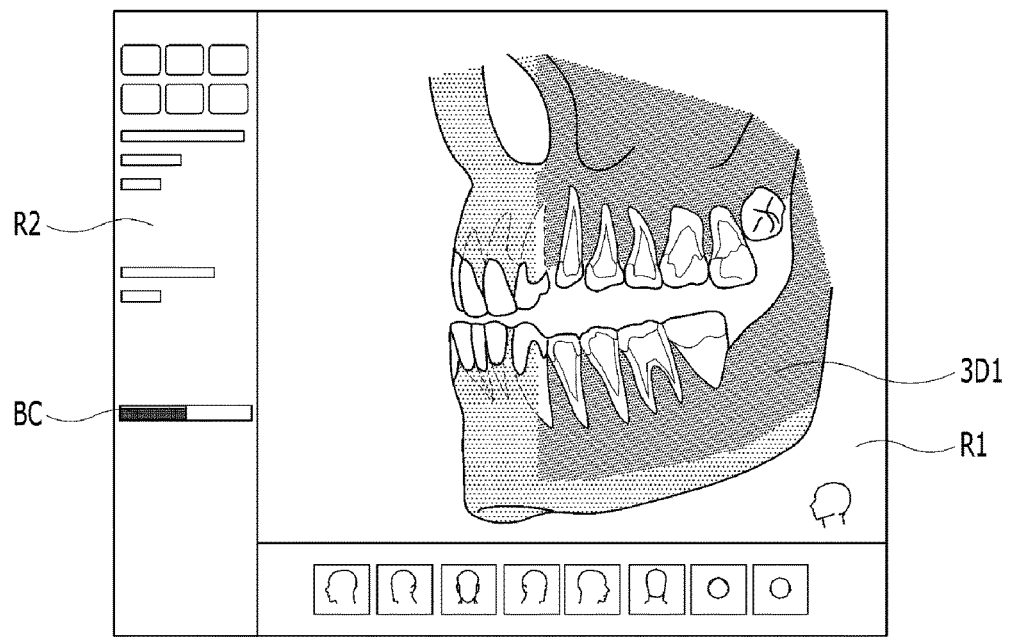
[Fig. 12]
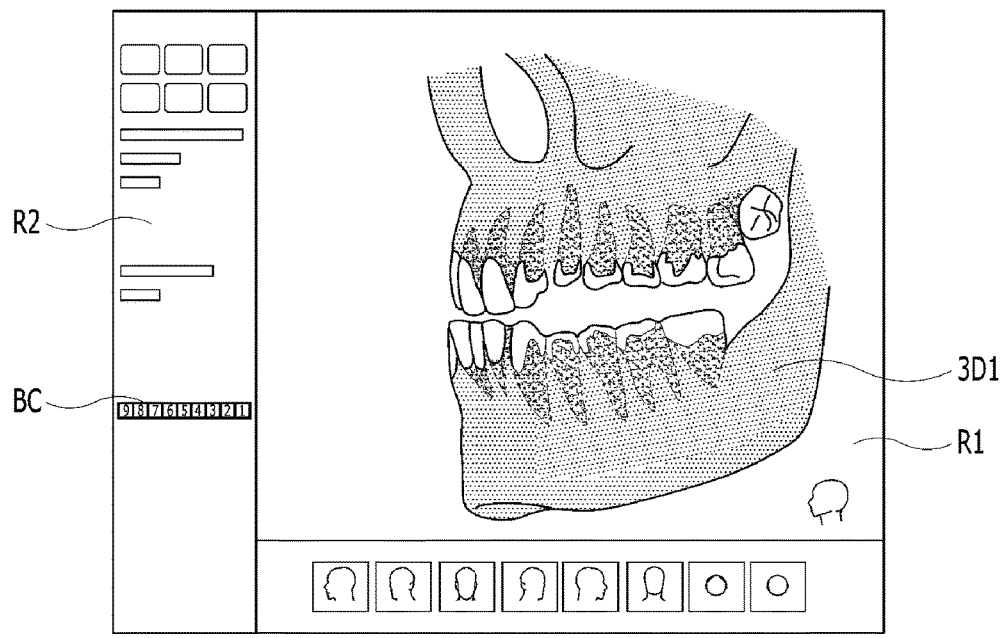

[Fig. 13]
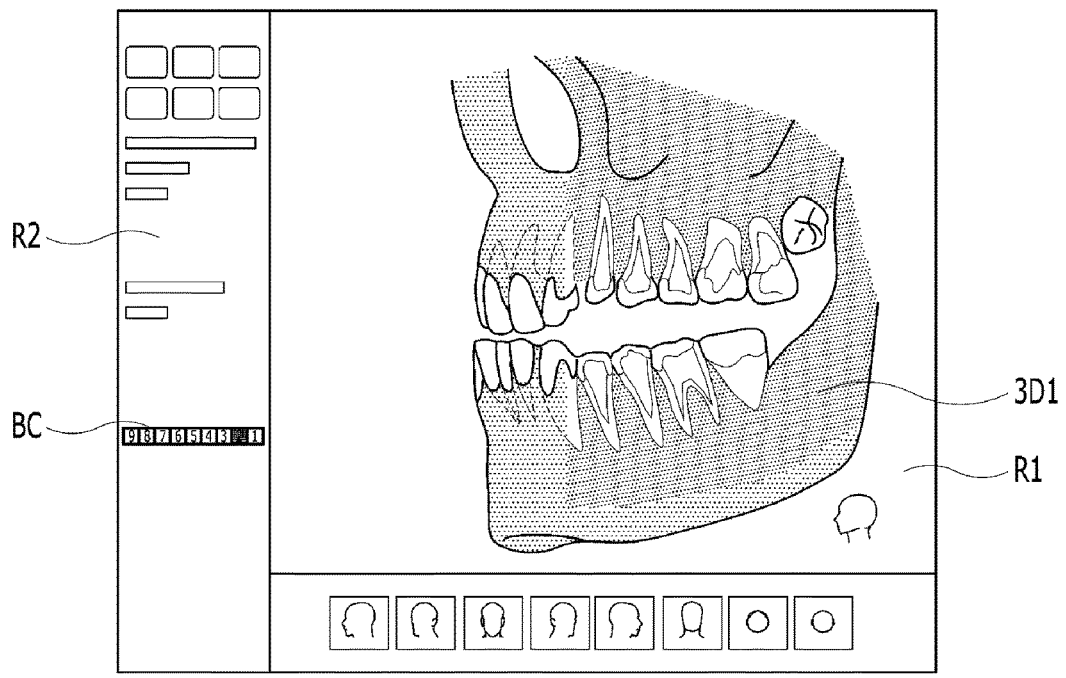
[Fig. 14]
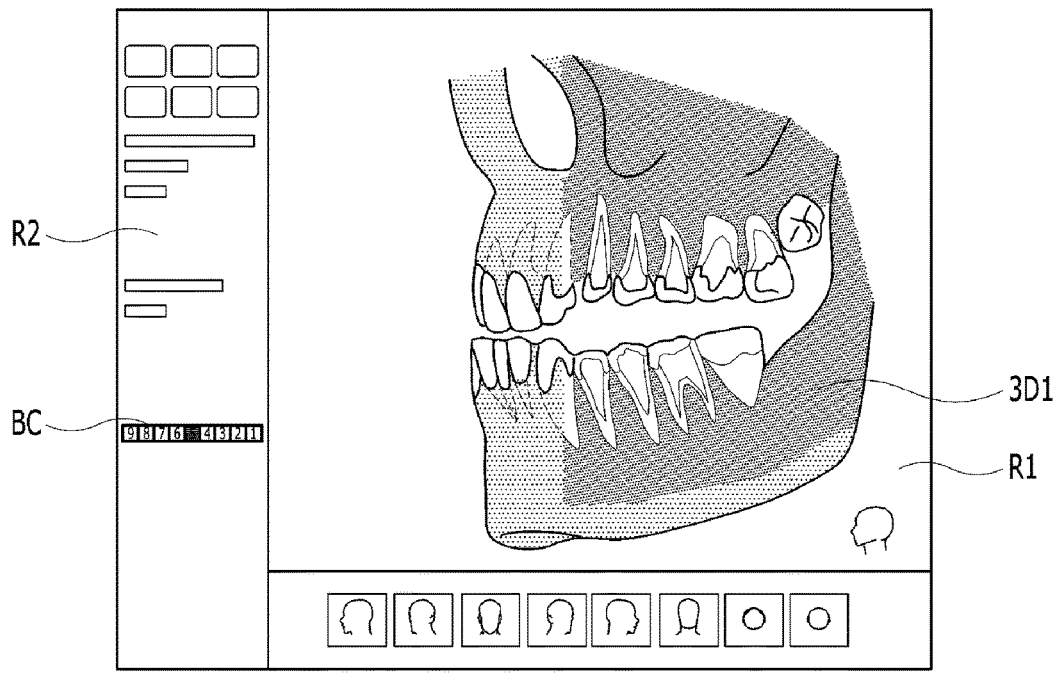

[Fig. 15]
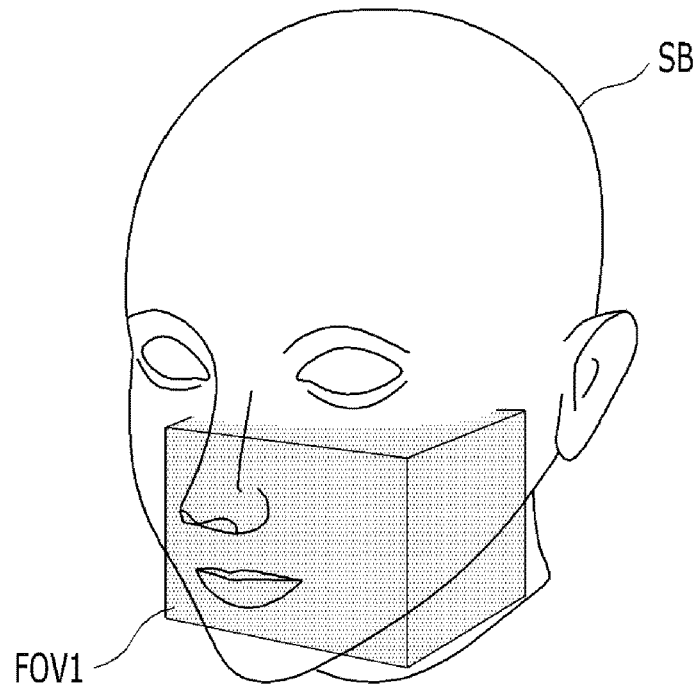
[Fig. 16]
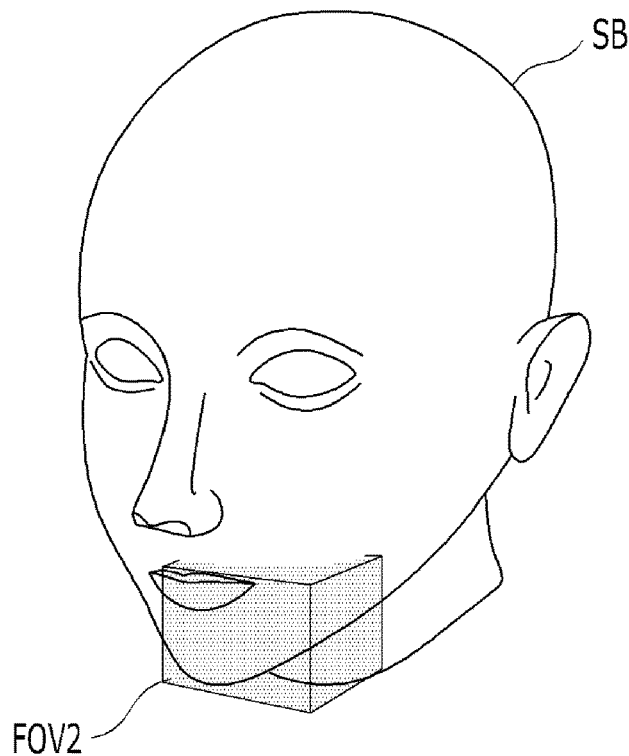

DISPLAYING 3D IMAGE WITH A PLURALITY OF SURFACE IMAGES AT DEPTHS OF INTEREST

CROSS REFERENCE TO RELATED APPLICATIONS

This application is a National Stage Patent Application of PCT International Patent Application No. PCT/KR2014/001081 (filed on Feb. 8, 2014) under 35 U.S.C. § 371, which claims priority to Korean Patent Application No. 10-2013-0014496 (filed on Feb. 8, 2013), the teachings of which are incorporated herein in their entireties by reference.

TECHNICAL FIELD

The present disclosure relates to an image display, and more particularly to an image display to display internal structures within an image with variation of depth of views.

BACKGROUND ART

An X-ray computerized tomography (CT) imaging apparatus emits X-rays to an object and detects the X-rays transmitted through the object using an X-ray detector. Based on the detected X-rays, the X-ray CT imaging apparatus generates image data. The X-ray CT imaging apparatus produces and displays a three-dimensional (3D) image and internal structure of the object based on the generated image data.

FIG. 1 to FIG. 5 illustrate dental X-ray images in three dimensions (i.e., 3D image) produced and displayed by a typical image display apparatus. As shown in FIG. 1, the typical image display apparatus may produce and display a volume image of a dental arch of a patient. Based on such a volume image (i.e., 3D dental image), a user, such as a dentist, examines a tooth including a dental crown extending from a gum and a dental root covered with the gum. In order to examine the dental root with the volume image, the user manipulates the volume image as follows. The user rotates the volume image so as to see a bottom of the dental arch, as shown in FIG. 2. The user designates a region to be deleted in order to see a dental root of interest, as shown in FIG. 3. The user deletes the designated region, as shown in FIG. 4. The user rotates the volume image to see the dental roots of interest revealed after the deletion, as shown in FIG. 5.

To see the dental roots of interest with the typical display apparatus, the user generally performs at least three steps of: i) rotating the volume image, ii) designating the region to be deleted, and iii) rotating the volume image after deletion of the designated region, as described. In addition, the user should be accustomed to using the typical display apparatus. Even if the user is proficient in using the typical apparatus, it is not easy for the user to designate the region to be deleted accurately to a depth to be examined. From time to time, the user returns to and restores the entire volume image in order to change the region of interest with another region of interest. In this case, all the three steps should be performed again one after another, and which is time consuming.

DISCLOSURE OF INVENTION

Technical Problem

Manipulation of an image, such as a dental image, between several views to focus on a particular area of one of the teeth in interest requires a user to perform many steps before obtaining the desired image. Such excessive steps in manipulation requires time, skill and training on the part of the user, and increases the possibility of error.

Solution to Problem

A volume image and a surface at a designated depth thereof may be shown by selecting a depth value based on a user input. From this point, via user input, a depth value can be selected, allowing the user to change the depth of view into the image.

In accordance with at least one embodiment, an image display apparatus may include a data storage, a processor, and an image display. The data storage may be configured to store image data. The processor may be configured to generate image data for a three dimensional (3D) image including internal surface images at one or more depths. The image display may be configured to display the 3D image with internal surfaces at each depth.

The 3D image may be an X-ray image. The X-ray image may be an image of a dental arch. The internal surface of the 3D image may include images of an internal structure of teeth including tooth root and an alveolar bone. The image display may display a model of a head and a field of view indication thereon.

In accordance with at least one embodiment, an image display apparatus may include a data storage, a user input interface, a processor, and an image display. The data storage may be configured to store image data. The user input interface may be configured to receive a request from a user. The processor may be configured to generate image data for a 3D image with internal surface images at one or more depths in response to the user request. The image display may be configured to display the 3D image with internal surfaces at each depth.

The image display may display a depth indicator including a scroll bar and a plurality of buttons. Based on user input received via the user input interface, a user may control the depth of the 3D image. The 3D image may be an X-ray image. The X-ray image may be of a dental arch. At least one internal surface of the 3D image may show an internal structure of teeth including tooth root and an alveolar bone. The image display may display a model of a head and a field of view indication thereon.

In accordance with at least one embodiment, a method may be provided for display images. The method may include displaying a three dimensional (3D) image, receiving a user request, and displaying a 3D image with internal surface images at one or more depths in response to the user request.

Advantageous Effects of Invention

A user does not require substantial skill or training to obtain appropriate images in association with one another for diagnosis and treatment, while also reducing the time required to obtain the desired image.

BRIEF DESCRIPTION OF DRAWINGS

The accompanying drawings, which are incorporated in and constitute a part of this specification, illustrate one or more embodiments described herein and, together with the description, explain these embodiments. In the drawings:

FIG. 1 to FIG. 5 are schematic diagrams showing a procedure to examine dental roots with 3D images displayed on a typical X-ray image display device;

FIG. 6 is a schematic diagram showing an image display apparatus in accordance with at least one embodiment;

FIG. 7 is a schematic diagram showing explaining the image data of a CT image;

FIG. 8 is a schematic diagram showing a volume image displayed on an image display;

FIG. 9 to FIG. 11 are schematic diagrams showing surfaces as a change of a depth in accordance with at least one embodiment;

FIG. 12 to FIG. 14 are schematic diagrams showing surfaces as a change of a depth in accordance with at least one embodiment; and FIG. 15 and FIG. 16 are schematic diagrams showing a model of a head with a field of view.

BEST MODE FOR CARRYING OUT THE INVENTION

In accordance with an embodiment of the present invention, an image display apparatus includes: a data storage configured to store image data; a processor configured to generate image data for a three dimensional (3D) image including internal surface images at one or more depths; and an image display configured to display the 3D image with internal surfaces at each depth.

In accordance with another embodiment of the present invention, an image display apparatus includes: a data storage configured to store image data; a user input interface configured to receive a request from a user; a processor configured to generate image data for a 3D image with internal surface images at one or more depths in response to the user request; and an image display configured to display the 3D image with internal surfaces at each depth.

Mode for the Invention

The following detailed description refers to the accompanying drawings. The same reference numbers in different drawings may identify the same or similar elements. Also, the following detailed description does not limit the invention.

In accordance with at least one embodiment, a display device may produce and display a predetermined internal surface (e.g., a predetermined plane view) of an object according to a user input designating a depth thereof. Particularly, the display device may detect a user input to designate a depth of a three dimensional (3D) image. Based on the detected user input, the display device may produce and display an internal surface of the 3D image, which is corresponding to a depth indicated by the detected user input, without requiring further user inputs or user interaction. Hereinafter, overall configuration and operation of a display device will be described with reference to FIG. 6. For convenience and ease of understanding, the display device will be described as displaying a 3D image and internal surface views of dental structure. However, the present invention is not limited thereto. The display device may be applied to producing and displaying 3D image and internal surface views of any objects.

FIG. 6 illustrates a display device in accordance with at least one exemplary embodiment. Referring to FIG. 6, display device 100 displays a volume image (i.e., a three-dimensional (3D) image). Display device 100 may include data storage 110, image display 120, a user input interface 130, and a processor 140. The display device 100 may be configured and implemented via a typical computer, such as a laptop computer.

Data storage 110 may store 3D X-ray image data. The stored 3D X-ray image data may be generated based on image signals obtained from an X-ray computerized tomographic (CT) imaging apparatus. As an example, FIG. 7 illustrates the generation of 3D X-ray image data. As shown in FIG. 7, image signals may be obtained by emitting an X-ray to an object (OB) and detecting the X-ray transmitted through the object (OB) using an X-ray detector. The obtained image signals may be processed to generate the 3D X-ray image data. After the generation of 3D X-ray image data, the 3D X-ray image data may be stored in data storage 110. The 3D X-ray image data may include information on voxel values, CT numbers (e.g., Hounsfield scale), and information on surfaces in various directions. User input interface 130 represents one or more devices that allow a user to interact with the display device 100 such as, but not limited to, touch screen input, mouse input, and keyboard input. Advantageously, some embodiments employ a mouse input to select portions of the images on the screen for further processing.

In accordance with at least one embodiment, user input interface 130 is configured to receive various types of inputs, such as a request, from a user. For example, the inputs (e.g., request) may include inputs for changing a direction (e.g., a display direction) of volume X-ray image 3D1, for changing a depth of an internal surface, and for displaying internal surfaces one by one. User input interface 130 may include a mouse, a key board, a touch pad, and a touch panel disposed on a screen of image display 120. User input interface 130 may be combined with image display 120. That is, the user may move a cursor or an indicator displayed on the screen of image display 120 in order to control the display direction. Furthermore, user input interface 130 may receive inputs for scrolling or for activating (e.g., touching or clicking) a menu bar or tool bars displayed on the screen in order to receive the information on the depth of surface to be examined.

Processor 140 may produce a CT image of the object (OB) based on the 3D X-ray image data stored in data storage 110 and a user input detected by user input interface 130. For example, processor 140 may produce 3D image data based on the user input made through user input interface 130.

Image display 120 may receive 3D image data from processor 140 and display a 3D image on the screen. Image display 120 may provide first region R1 for displaying 3D images and second region R2 for displaying menu bars and toolbars. As shown in FIG. 8, image display 120 may display volume X-ray image 3D1 within first region R1 on the screen, based on the 3D mage data received from processor 140.

Furthermore, image display 120 display volume X-ray image 3D1 rotatable about an axis (not shown) according to a display direction controlled or appointed by a user.

Processor 140 may generate 3D image data with the 3D X-ray image data stored in data storage 110 based on user inputs or requests received through user input interface 140. Such user inputs may include information for controlling or manipulating the 3D image displayed on the screen of image display 120. For example, in response to a user input for controlling a direction for rotation (e.g., rotation direction), processor 140 may generate 3D image data to display corresponding volume X-ray image 3D rotating according to the rotation direction as shown in FIG. 9. When a user designates a depth through user input interface 140 (e.g., entering information on a depth of interest), processor 140 may generate the 3D mage data to display a surface (e.g., a sectional plane view) at the designated depth, as shown in FIG. 10. When a user requests displaying an internal surface, processor 140 may generate the 3D image data for displaying a 3D image with an internal surface at each depth, one by one depth value (e.g., by a predetermined interval), as shown in FIG. 10 and FIG. 11.

For example, a user may input the depth information by scrolling menu bar BC displayed in second display region R2, as shown in FIG. 9 to FIG. 11. In this case, processor 140 may determine a depth value based on the amount of movement of the scroll. In accordance with at least one exemplary embodiment, the length of the menu bar may be proportional to the number of voxels from a contour surface of volume image 3D1 to a predetermined surface (e.g., the deepest surface) in a direction to be examined. According to the scroll amount, the processor 140 determines an associated depth (e.g., associated voxel value) and generates the 3D image data so as to show the surface (e.g., a contour surface, a sectional view image, or a sagittal plane view) at the determined depth. Accordingly, display device 100 may allow a user to conveniently, clearly, and efficiently examine the internal dental structure including a tooth root, a cementum, an alveolar bone, and so forth by changing a depth through scrolling menu bar BC. In accordance with another embodiment, the user may designate the depth by selecting one of depth indication buttons 1 to 9 shown in FIG. 12 to FIG. 14. The depth indication buttons correspond to the respective depths ranging from i) the contour surface of volume image 3D1 to ii) the deepest surface of a dental arch thereof. The number of the depth indication buttons may depend on a depth difference between adjacent buttons. In other words, the number of the buttons may be determined in consideration of ease of use. For a detailed analysis, the number may be increased to a maximum number of the voxels in the direction to be examined.

In accordance with still another embodiment of this invention, a user may be enabled to designate a region of interest in an object. By designating the region, display device 100 may produce and display internal surfaces of the designated region according to a depth controlled or selected based on a user input made through user input interface 140. For example, a user might select a particular tooth for careful examination. Display device 100 may produce and display internal surfaces (e.g., sectional image views) of the designated tooth. In accordance with yet another embodiment, display device 100 might display a field of view (FOV) on a model of a head, as shown in FIG. 15 and FIG. 16, where the FOV is changed from a relatively large area (FIG. 15) to a relatively small area (FIG. 16). Namely, the model of head shown in FIG. 9 to FIG. 11 and FIG. 12 to FIG. 14 may be displayed with the FOV so that the user is shown the position and the size of the FOV.

According to this invention, a volume image and a surface at a designated depth thereof may be shown by selecting a depth value based on a user input. From this point, via user input, a depth value can be selected, allowing the user to change the depth of view into the image.

Thus, the user does not need to improve his skill to obtain appropriate images in association with one another for diagnosis and time for obtain appropriate can be reduced effectively.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implentation."

As used in this application, the word exemplary is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Moreover, the terms "system," "component," "module," "interface," "model" or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

The present invention can be embodied in the form of methods and apparatuses for practicing those methods. The present invention can also be embodied in the form of program code embodied in tangible media, non-transitory media, such as magnetic recording media, optical recording media, solid state memory, floppy diskettes, CD-ROMs, hard drives, or any other machine-readable storage medium, wherein, when the program code is loaded into and executed by a machine, such as a computer, the machine becomes an apparatus for practicing the invention. The present invention can also be embodied in the form of program code, for example, whether stored in a storage medium, loaded into and/or executed by a machine, or transmitted over some transmission medium or carrier, such as over electrical wiring or cabling, through fiber optics, or via electromagnetic radiation, wherein, when the program code is loaded into and executed by a machine, such as a computer, the machine becomes an apparatus for practicing the invention. When implemented on a general-purpose processor, the program code segments combine with the processor to provide a unique device that operates analogously to specific logic circuits. The present invention can also be embodied in the form of a bitstream or other sequence of signal values electrically or optically transmitted through a medium, stored magnetic-field variations in a magnetic recording medium, etc., generated using a method and/or an apparatus of the present invention.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

As used herein in reference to an element and a standard, the term "compatible" means that the element communicates with other elements in a manner wholly or partially specified by the standard, and would be recognized by other elements as sufficiently capable of communicating with the other elements in the manner specified by the standard. The compatible element does not need to operate internally in a manner specified by the standard.

Although embodiments of the present invention have been described herein, it should be understood that the foregoing embodiments and advantages are merely examples and are not to be construed as limiting the present invention or the scope of the claims. Numerous other modifications and embodiments can be devised by those skilled in the art that will fall within the spirit and scope of the principles of this disclosure, and the present teaching can also be readily applied to other types of apparatuses. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

INDUSTRIAL APPLICABILITY

The present invention is applicable to display internal structures within an image with variation of depth of views.

The invention claimed is:

1. An image display apparatus comprising:

a data storage configured to store image data of a target object for displaying the target object in a three dimensional (3D) X-ray image;

a processor configured to receive a user input designating a region of the target object on the 3D X-ray image, a change in direction of the 3D X-ray image, and a depth information, determine a depth based on the depth information according to the change in direction of the X-ray image, and generate 3D X-ray image data of the target object using the stored image data and surface image data of a plurality of internal surface images at a predetermined interval of the input region; and an image display configured to display the 3D X-ray image and the plurality of internal surface images using the 3D X-ray image data one by one at the predetermined interval including the determined depth in response to the user request.

2. An image display apparatus according to claim 1, wherein the 3D X-ray image is an image of a dental arch.

3. An image display apparatus according to claim 1, wherein the plurality of internal surface images of the 3D X-ray image include images of an internal structure of teeth including tooth root and an alveolar bone.

4. An image display apparatus according to claim 1, wherein the image display displays a model of a head and a field of view indication thereon.

* * * * *